United States Patent [19]
Eden et al.

[11] Patent Number: 5,342,510
[45] Date of Patent: * Aug. 30, 1994

[54] WATER CONTROL SYSTEM USING OXIDATION REDUCTION POTENTIAL SENSING

[75] Inventors: Todd R. Eden, Scottsdale; Jerome H. Ludwig, Paradise Valley, both of Ariz.

[73] Assignee: h.e.r.c. Incorporated, Phoenix, Ariz.

[*] Notice: The portion of the term of this patent subsequent to Dec. 7, 2010 has been disclaimed.

[21] Appl. No.: 99,737

[22] Filed: Jul. 30, 1993

Related U.S. Application Data

[63] Continuation-in-part of Ser. No. 59,514, May 17, 1993, Pat. No. 5,268,092, which is a continuation of Ser. No. 829,762, Feb. 3, 1992, abandoned.

[51] Int. Cl.$^5$ .............................................. B01D 17/12
[52] U.S. Cl. ................................... 210/96.1; 204/433; 210/198.1; 210/700; 324/438
[58] Field of Search ............ 210/85, 96.1, 143, 198.1, 210/696, 698, 700, 699, 743, 746, 764; 204/406, 433, 153, 21; 324/71.1, 71.5, 438; 137/5, 93; 134/22.14, 22.19, 56 R

[56] References Cited

U.S. PATENT DOCUMENTS

| | | | |
|---|---|---|---|
| 3,308,161 | 3/1967 | Shen | 210/698 |
| 3,627,032 | 12/1970 | Glad | 55/228 |
| 3,628,663 | 12/1970 | Derham | 210/151 |
| 3,788,340 | 1/1970 | O'Leary | 261/70 |
| 3,805,880 | 4/1974 | Lawlar | 210/700 |
| 3,825,483 | 7/1974 | Nakamura | 204/406 |
| 4,464,315 | 8/1984 | O'Leary | 137/93 |
| 4,767,511 | 8/1988 | Aragon | 210/746 |
| 4,836,239 | 6/1989 | Kinkead | 62/171 |
| 4,931,187 | 6/1990 | Derham | 210/742 |
| 4,963,815 | 10/1990 | Hafeman | 324/71.5 |
| 5,218,304 | 6/1993 | Kinlen et al. | 324/438 |
| 5,259,985 | 11/1993 | Nakanishi et al. | 210/700 |

*Primary Examiner*—Joseph W. Drodge
*Attorney, Agent, or Firm*—Wood, Herron & Evans

[57] ABSTRACT

An automatic control system for maintaining the quality of water in a cooling tower utilizes a probe (38) which senses the oxygen reduction potential (ORP) of a soap having a 1:1 stoichiometric equivalent of an organic acid and ammonia in the water. The soap is pumped from a chemical supply means (20) containing the soap in response to the ORP of the soap in the water falling below a predetermined threshold. A second sensing probe measures the conductivity (in MHos) of the water as a factor of the total dissolved solids (TDS) to control the bleed-off or blow-down of the water. The chemicals, which are supplied for maintaining the ORP, permit significantly higher total dissolved solids in the water than with standard cooling tower systems, without the buildup of scale. As a consequence, water consumption is significantly reduced; and the system functions automatically, without requiring periodic visual inspection, water analysis or manual operation.

11 Claims, 1 Drawing Sheet

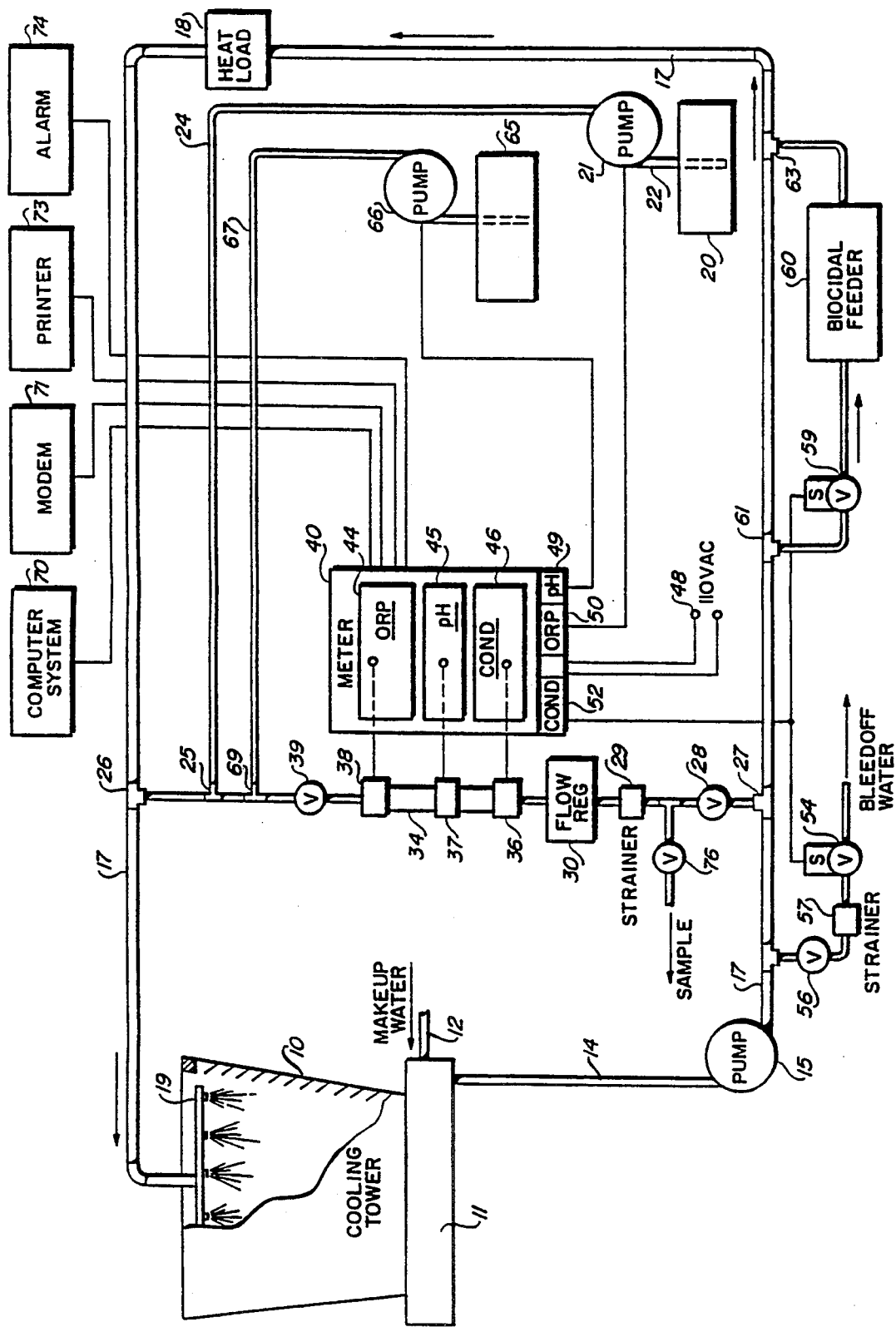

WATER CONTROL SYSTEM USING OXIDATION REDUCTION POTENTIAL SENSING

RELATED APPLICATION

This application is a continuation-in-part of application Ser. No. 059,514 filed May. 17, 1993, now U.S. Pat. No. 5,268,092, which is a continuation of application Ser. No. 829,762 filed on Feb. 3, 1992, now abandoned, both assigned to the same assignee as the present application. Also related is application Ser. No. 700,780, filed May. 16, 1991, and the disclosure of that application is incorporated herein by reference. This application is also related to application Ser. No. 08/099,738, filed on even date herewith.

BACKGROUND

Water cooling towers are in widespread use for large capacity heat exchange systems. These cooling towers are used to remove absorbed heat from a circulating water coolant by evaporating a portion of the coolant in the cooling tower. The remaining coolant is extracted from a reservoir or sump at the base of the tower by a pump, and supplied through the heat load on a continuous basis. Because a large quantity of water evaporates in such a system, a significant and fairly rapid build-up of scale, sludge and the like takes place in the water. Various chemicals are employed preventing the precipitation out of the minerals in the water, since such precipitation causes what is known as "scaling" on the surfaces of the cooling tower and heat exchange equipment. If such scaling is not prevented or is not periodically removed, it can result in significantly reduced heat transfer, and, therefore, significantly increased operating costs. In addition, it enhances corrosion of the heat exchange surfaces beneath the scale.

In addition to the scaling problem mentioned above, if the pH factor in the water is too low (typically, below 6.8), increased corrosion of the system components can result. If the pH is too high, the significant scale build-up mentioned above, takes place. Consequently, it has been the practice to add chemicals to the cooling tower water to maintain a balanced or "safe" range of pH factor in the coolant.

Even with the addition of chemical additives to maintain a chemical balance in the coolant water, the constant significant evaporation of a portion of the water rapidly builds up the amount of total dissolved solids (TDS) in the water to the point where scaling can occur, even though scale-retardant chemicals are present in the water. To prevent scaling from occurring, it is customary periodically to remove water with a high TDS content from the system to reduce the TDS, or to increase the oxidizing potential or pH. When water is removed, it is replaced with "make-up" water, which typically is obtained from the local available or modified water supply. The removal or dumping of water from the system is accomplished in one or the other of two ways, namely a "bleed-off" in which a portion of the sump or reservoir water is drained while the system is operating, or by "blow-down", which typically is a complete draining of the sump. In both cases, the water which is drained off is replaced with the "make-up" water.

Typically, the dumping of water by either "bleed-off" or "blow-down" in cooling tower systems, is effected when the TDS is somewhere around 5,000 ppm. In most systems, a TDS in excess of 5,000 ppm results in scaling, even with the use of chemical additives and oxidants.

In the past, the decision to initiate dumping of water from the reservoir of the cooling tower generally has been manually determined. In some cases, such dumping simply is done on a periodic basis. In other cases, a visual inspection of the water in the cooling tower is made to determine whether or not to effect dumping of some of that water. This is a very imprecise technique, and typically results in the dumping of excessive quantities of water from the system.

A system, which has been developed for providing a somewhat more precise control of the dumping or bleed-off of water from a cooling tower system, is disclosed in the patent to O'Leary U.S. Pat. No. 4,464,315. This patent includes probes for sensing the conductivity of the cooling tower water, as well as the conductivity of the make-up water. The probes provide signals to a controller unit, which proportionally adjusts the trip point at which dumping of the cooling tower water occurs, based upon the sensed water conductivities. A problem with a system of the type disclosed in the O'Leary patent, however, is that at TDS concentrations of 5,000 ppm or less, the differences in conductivity at different TDS concentrations are relatively small; so that accurate determination of the concentration required for dumping of water is difficult. In addition, for such low TDS concentrations, frequent dumping, either by way of blow-down or bleed-off, is required, resulting in the waste of substantial quantity of water.

The water which is dumped from a cooling tower system represents a significant loss. In a typical, relatively small and relatively efficient evaporative cooling tower system, a total amount of approximately 637,000 gallons per year of water is consumed by the cooling tower. Of this amount, 437,000 gallons are evaporated in the cooling process. The other 200,000 gallons is flushed down the sewer in the bleed-off operation. This ratio, of approximately one-third of the total amount of water used being totally wasted, is typical of such systems. Some cooling tower systems waste an even greater quantity of water. Not only does this wasted water result in an appreciable loss, both in the resource of the water itself, and in its cost; but most cooling tower systems use chemicals or additives, such as acids, anti-fouling agents and corrosion inhibitors, to prevent corrosion and scaling from occurring. These chemicals constitute a substantial environmental risk, since in many cases the chemicals are toxic and/or hazardous.

The patent to Derham, U.S. Pat. No. 4,931,187 discloses another cooling tower system in an effort to automate control of pH, temperature and TDS. In the Derham system, these parameters are monitored to control the addition of make-up water to the cooling tower, either by means of a bypass or through a water softener, or both, in accordance with the different variables measured by the system. Derham states that the system eliminates virtually any bleed-off of coolant. To accomplish this, however, an additional particle filter must be included to remove suspended solids from the coolant. It is necessary, however, to backwash the filter with water from outside the system on a periodic basis. It is not clear how scaling can be prevented without any dumping of the water recirculated in the cooling tower system, since at some point the TDS in that water reaches a saturation point. While some precipitated solids will be removed by the filter 20, it appears that scaling also can occur as a result of saturation, irrespective of the operation of the water softener and the filter. These additional components also require extra periodic maintenance for their operation.

Other cooling tower systems have been designed, which include an automatic pre-established timer control of backwash and chemical addition (Derham U.S. Pat. No. 3,628,663) or some type of float responsive to the water level in the cooling tower for controlling either make-up water addition (Kinkead U.S. Pat. No. 4,836,239), or make-up water addition and chemical addition (O'Leary U.S. Pat. No. 3,788,340 and Glad U.S. Pat. No. 3,627,032).

In addition to corrosion and scaling conditions, materials are introduced through air, water and environmental changes, which provide sources for biological support of aerobic or anaerobic algae and the like. While, to some extent, suspended solids in the water may provide a visual indication of the existence of undesirable biological conditions, typically, the conditions are not discernable to the viewer until a critical condition exists.

It is desirable to provide automatic control of the electron equilibrium of the water in a system, to significantly reduce the amount of water which must be dumped from the system, to accurately sense the conditions required for the addition of chemical additives, with a minimum of maintenance or supervision in its operation.

SUMMARY OF THE INVENTION

This invention is directed to an automatic control system adapted for controlling scale formation in a water circulating system, comprising:

first sensing means for measuring the oxygen reduction potential (ORP) of the circulating water containing a soap having a 1:1 stoichiometric equivalent of an organic acid and ammonia base in the water for controlling scale formation in said system and supply means for automatically supplying said soap in response to a predetermined ORP measured by said first sensing means substantially corresponding to a pH higher or lower than a selected range for controlling said scale.

In the above-identified applications Ser. Nos. 829,762 and 059,514, a soap of an organic acid and an amine has been disclosed as an additive for controlling scale in circulating water employing an automatic control system by measuring the oxygen reduction potential (ORP) of the water containing the soap and supplying soap upon demand. It has now been found that soaps of an organic acid and ammonia can also be employed in the automatic control system.

It is an object of this invention to provide an improved water system.

It is an additional object of this invention to provide an improved automatic control of the operation of a water system.

It is another object of this invention to provide an improved control system for a water system for automatically monitoring the conditions required for adding chemical additives to the water, and effecting the addition of such additives to control various parameters affecting the water quality.

It is a further object of this invention to provide an improved water system for effectively controlling the dumping of water from the system in response to the conductivity of the water, and for automatically adding chemical additives to the water in response to a sensed condition of the water.

In accordance with a preferred embodiment of the invention, an automatic control system for a water system includes a first sensor (ORP sensor) for measuring the oxygen reduction potential (REDOX) of the water recirculated in the water system. A reservoir for the soap of an organic acid and ammonia is coupled with the ORP sensor to supply the soap to the water whenever a pre-established ORP is measured by the ORP sensor. Another sensor measures the conductivity of the water, as a factor of total dissolved solids (TDS). Whenever the conductivity (measured in mHos) of the cooling tower water (representative of TDS) reaches a pre-established conductivity, water is removed or dumped from the system.

BRIEF DESCRIPTION OF THE DRAWING

The sole FIGURE of the drawing is a diagrammatic representation of a preferred embodiment of the invention.

DETAILED DESCRIPTION

Before entering into a description of the operation of the system shown in the drawing, a brief discussion of ORP measurement is in order. ORP is a measurement of the electron exchange potential which occurs in an ionic reaction, Since most heat transfer systems, including cooing tower systems, are constructed of metal, utilizing ever-changing water, there typically is an undesired equilibrium created. The ORP measurement allows control of the electrochemical equilibrium. Chemical equilibria determines whether the stable form of a material is soluble or insoluble. If soluble species of material are stable, it is possible for a metal rapidly to corrode into aqueous forms. If insoluble species of material are stable, there is a tendency to form a scale, inhibiting corrosion, but inducing "under scale" corrosion. Both corrosion and scale are undesirable conditions in a cooling tower system, since degradation of the system operation occurs when either of these conditions are present to any substantial extent.

Two terms commonly used in chemistry and important to note from the standpoint of corrosion are oxidation and reduction. Oxidation may be difficult to pinpoint, since according to corrosion terminology, it can mean either the rusting of iron or the development of white oxides on aluminum or zinc. In order to understand their meanings from a chemical standpoint, it is necessary to examine a chemical formula such as that for iron:

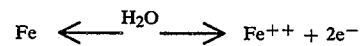

$$Fe \xleftarrow{\quad H_2O \quad} Fe^{++} + 2e^-$$

This formula indicates iron in water in a state of equilibrium where no current flow exists. The "Fe" is iron as a metal, the "Fe++" is the ionized form of iron, and the electrons indicate the negative charges given up when the metal changes to an ion. The movement of the iron from the metal form to the ion form is called oxidation. Therefore, in a corrosion cell, the metal is oxidized when it goes into solution as an ion. This occurs at the anode where the term oxidation also commonly applies to rust forms.

When proceeding in the opposite direction and adding electrons to the ionized iron, the reaction occurs in the direction of the iron as metal, and is referred to as reduction. A metal, therefore, which has been changed from its oxidized state to the metal, has been reduced. This is what takes place when iron ore is changed to metal in a blast furnace.

Different metals have different capacities for being reduced and for being oxidized. Gold, for example, exists primarily in the reduced state, e.g., as a metal. Potassium, on the other hand, exists primarily in either the oxidized state as an oxide or in the ionic state as a salt. The symbolic reaction for iron given above and its relative potential for the electrochemical reactions known is called an oxidation-reduction potential. It may also be called a redox potential, half-cell potential, or solution potential.

The benefit of ORP measurement is that when it is calculated properly, it permits maintenance of a system such as a cooling tower system, within operable, ideal parameters, in the operation of the preferred embodiment described subsequently, it has been found that to control corrosion or scaling, the oxidation potential must be controlled. The oxidation electrochemical reaction produces an electron flow which can be measured through ORP measurement probes. This measured potential then may be utilized to effect the introduction of controlled quantities of additives to control corrosion or scale, regardless of changing environmental conditions. ORP measurements also are affected by other variables, including biological; so that the analysis of changing environmental factors can be controlled through ORP instrumentation. This is accomplished by the system disclosed in the drawing.

Reference now should be made to the drawing, which illustrates a preferred embodiment of the invention. The embodiment shown in FIG. 1 functions to permit up to 30,000 ppm TDS concentration (measured as 0 to 100,000 mHos) in the water recirculated in a cooling tower system without scale or corrosion. This is accomplished by the use of chemical additives of the type disclosed in the above identified copending applications which are incorporated herein by reference, to control the quality of the water. The additives of the present invention preferably comprise aqueous solutions of 1:1 stoichiometric soaps of an organic acid, such as a carboxylic or sulfonic acids, and ammonia. These soaps are effective in solubilizing magnesium and calcium carbonate, which are predominate constituents of water scale/deposit. The concentration levels of the chemical additives are measured by measuring the ORP (oxygen reduction potential) of the water containing the additives.

A conventional cooling tower 10 is shown. The cooling tower 10 has a sump or reservoir 11 at its bottom, with a pipe 12 for introducing make-up water whenever the water level in the sump 11 drops below some minimum level. A pump 15 withdraws the water from the reservoir 11 through a pipe or conduit 14, and supplies that water through another pipe or conduit 17 to a heat load 18, from which the water continues through the pipe 17 to spray nozzles 19 located in the top of the cooling tower 10. The system described thus far is a conventional cooling tower system, and may be constructed in a variety of different standard configurations.

In the system shown in the drawing, a reservoir 20 for a liquid chemical additive is indicated, with a pump 21 located to withdraw chemicals from the reservoir 20 through a pipe 22, and supply those chemicals through a pipe 24 and an injection T 25 and a T 26 to the water recirculating through the conduit or pipe 17. In systems of the prior art, the pump 21 typically would be operated in response to a manually activated control at such times and for such durations as determined by an observer of the water quality recirculating through the system.

In the system disclosed in the drawing, however, control of the pump 21 is effected through a meter/monitoring unit 40. The inputs to the monitoring unit 40 are provided from an ORP probe 38, a pH probe 37 and a conductivity probe 36 located in a measuring section 34 of a shunt line connected between a T 27 and the T 26. A valve 28 is located between the T 27 and a strainer 29 to supply water in the shunt through a flow regulator 30 to establish a constant flow rate; so that the measurements made by the probes 36, 37 and 38 are constant, irrespective of changing flow conditions which may take place in the conduit 17. At the outlet side of the unit 34 is another valve 39. The valves 28 and 39 typically are manually controlled valves, which are normally open; so that the shunt is constantly operated to bypass small amount of the water supplied from the pump 15 through the shunt for the measurement by the probes 36, 37 and 38. All of the water which passes through the section 34 is returned to the recirculating water in the system by means of the T 26.

The probe 38 is a standard ORP probe (such as TBI model 540) manufactured by TBI-Baily controls), and it supplies ORP voltage or potential measurements to the ORP monitoring/comparison section 44 in the unit 40. The measured potentials typically are characterized as oxidation potentials, since the magnitude of the measured potential from the probe 38 is representative of the relative ease with which reductants in the water oxidize. It has been found that measurement of ORP provides a more accurate indication of the condition of the water than a measurement of pH, since pH is difficult to adjust in a system of the type shown in the drawing in which the water has very high TDS. As mentioned above, an ideal composition for the additive in the reservoir 20, for effecting the removal and prevention of scale in the cooling tower water, has been found to be a composition containing a 1:1 stoichiometric equivalent of an organic carboxylic acid and ammonia according to this invention. Various organic acids and ammonia may be used in accordance with this invention.

Whenever a condition is sensed by the ORP probe 38, indicative that additional chemical additives need to be supplied to the recirculating water in the system, the comparison section 44 operates an ORP output switch 50 to provide a signal to a pump 21 to operate the pump to withdraw additive through the pipe 22 from the reservoir 20. This operation continues until the ORP potential measured by the probe 38 returns to a "safety" range of potential. At that time, the ORP switch 50 is once again opened, and the pump 21 ceases operation.

The pH probe 37 is optional, but may be used in addition to the ORP probe 38 to control the addition of acid to the water from a reservoir 65. If low acidic conditions are sensed by the probe 37, a signal is supplied to a monitoring/comparison section 45 in the unit 50. The section 45 operates a pH switch 49 to provide a signal to a pump 66. The pump 66 withdraws acid from the reservoir 65 and supplies it through a pipe 67 to a T 69, where the acid is added to the recirculating water in the system. This operation continues until the pH sensed by the probe 37 is correct. The switch 49 then is opened, and the pump 66 is turned off.

When the chemical additive contains a 1:1 stoichiometric soap equivalent, as described above, applicant has found that the TDS (total dissolved solids) in the water, which can be reached without scaling or corrosion, are significantly higher than the 5,000 ppm typical of conventional cooling tower systems. TDS concentrations of 30,000 ppm, or higher, (measured as 0 to 100,000 mHos) can be attained by the system without requiring dumping by way of either bleed-off or blow-down of the water from the cooling tower reservoir. Consequently, the conductivity sensor 36 coupled to the unit 40 is set to measure conductivity produced by these significantly higher TDS levels. Since the TDS level of the water can be an order of magnitude or more than can be tolerated in conventional systems a much more sensitive or accurate conductivity probe 36 may be employed. Whenever the TDS level reaches a level of for example 30,000 ppm, a signal is provided by the conductivity probe 36 to the comparison section 46 to cause a conductivity switch 52 to be closed. This supplies a signal to operate a solenoid-controlled valve 54 located in a bleed-off shunt from the conduit 17. The bleed-off is effected through a normally open manual valve 56 and a strainer 57 to dump the bleed-off or blow-down water from the reservoir 11 of the cooling tower. The strainer 57 is provided to prevent silt and other particles from interfering with the proper operation of the valve 54.

The operation of the conductivity switch 52 may be effected until the conductivity sensed by the probe 36 drops to some second lower predetermined value, whereupon the switch 52 is opened to turn off the valve 54. This is a typical operation for a "bleed-off" dumping of water from the system while it is continuously running. Obviously, make-up water through the pipe 12 will be provided to the sump 11, as soon as the water level drops to some minimum value, as described above, as a result of the dumping of water through the valve 54.

Operation of the switch 52 may be used to coordinate the operation of the valve 54 with a sensor or float in the reservoir and another valve (not shown) between the water supply and the pipe 12 illustrated in the drawing. In this condition, all of the water in the sump could be dumped, if desired, (blow-down). After this has been accomplished, as measured by the float in the reservoir 11, the valve 54 is once again closed, and make-up water is permitted to be supplied to the sump 11 through the pipe 12.

Whenever there is a bleed-off or a blow-down of water from the reservoir 11, an initial significant imbalance of the chemical condition of the water occurs as a result of replacement of a substantial quantity (or replacement of all) of the water in the cooling tower system. Consequently, an additional solenoid-controlled valve 59 and a biocidal feeder 60 also preferably are provided to biologically shock the system simultaneously with the operation of the blow-down or bleed valve 54. The valve 59 is operated by the switch 52 with the valve 54.

The additives, described above, as supplied from the reservoir 20, are not affected when the chemicals in the biocidal feeder are quaternary ammonia compounds. Thus, if such compounds are provided in the biocidal feeder 60, these compounds are mixed with water, which is diverted through the valve 59 from a T 61 to a T 63 to be added to the water circulating through the conduit 17. Quaternary ammonia is a non-oxidizing biocide for use in microbial suppression and destruction.

Oxidizing compounds, however, also can be supplied by the biocidal feeder 60 to obtain the desired microbial treatment. A typical preferred oxidizing compound contains bromine. Bromine compounds cause the ORP readings to increase significantly. This condition, however, is temporary, and normal operation of the ORP sensing and control resumes within a relatively short time after each "shock" treatment from the feeder 60.

The drawing also illustrates devices which may be coupled to the meter/monitor 40 for providing a record of the observed conditions established by the probes 36 and 38. For example, the signals which are continuously produced by the probes 36 and 38 may be supplied to a computer system 70 for processing, to a modem 71 for transmission to a remote location, or to a printer or plotter 73 to provide a continuous record of the conductivity and ORP being monitored. In addition, an alarm 74 may be provided to produce a visible or audible indication whenever either of the probes 36 and 38 provide an output indicative of an out-of-balance condition of the water recirculating through the cooling tower 10. These devices 70, 71, 73 and 74 are not necessary for the automatic operation of the system which has been described, but may be utilized in conjunction with that system to enhance its utility by monitoring its operation.

An additional valve 76 has been illustrated connected between the valve 28 and 29 in the shunt line to permit a sample of the water to be withdrawn from the system for test purposes. Normally, the valve 76 is closed; and water is only withdrawn infrequently for conducting analysis of the water quality which is not covered by the automatic system described above.

What has been discovered, is that ORP parameters, if set up correctly in the comparator or meter 44, analyze the solubility of the water with a millivolt reading output from the probe 38. Any element in the water, irrespective of its characteristics, affects the ORP. If the ORP reading raises, the solubility of the water increases. If the ORP reading lowers, the solubility decreases.

ORP is an electron activity measurement. This measurement is related to the pH of the water, and by maintaining the ORP within a safety range, currently arbitrarily independently calibrated at the set-up of each system operation, the pH remains between 6.8 and 8.5. Consequently, as long as the ORP is set, the only considerations which remain to be dealt with in the system are microbial corresponding to silt accumulation, biological activity and specific gravity. The table below illustrates the relationship between ORP readings (in millivolts) and pH, along with a designation of the cooling tower water conditions which produce corrosion and scaling.

TABLE 1

| pH | | ORP (millivolts) |
|---|---|---|
| 14 | | −1000 |
| | SCALING | |
| 8.5 | | −100 |
| | SAFETY ZONE | |
| 7 | | 0 |
| 6.8 | | +100 |
| | CORRODING | |

TABLE 1-continued

| pH | ORP (millivolts) |
|---|---|
| 0 | +1000 |

The ORP reading which correspond to pH of 6.8 and 8.5, respectively, initially must be independently calibrated for each system. It has been found that even when the same make-up water 12 is supplied to two identical systems side-by-side, ORP readings may vary considerably. Consequently, as the sump water concentrates with solids, ORP readings need to be determined which correspond with the pH readings of significance (typically, 6.8 and 8.5). Once these have been established, the comparator in the ORP meter 44 is adjusted accordingly to respond to these readings. The readings then remain consistent throughout the operation of the system; and fully automatic cooling tower system operation is possible. An ideal starting water condition is given below:

| CONDITION | MIN | MAX | |
|---|---|---|---|
| TEMPERATURE | 40° F. | 80° F. | |
| pH | 6.8 | 7.4 | |
| OXIDANT FREE & TOTAL | 0.0 | 1.5 | mg/L |
| TOTAL ALKALINITY | 60 | 180 | mg/L |
| TOTAL DISSOLVED SOLIDS | 500 | 1750 | ppm |
| CONDUCTIVITY | 750 | 2625 | mHos |
| TOTAL HARDNESS | 100 | 300 | mg/L |
| CALCIUM HARDNESS | 150 | 1000 | mg/L |
| DISSOLVED OXYGEN | 6 | 10 | mg/L |

The system which has been described above typically reduces the water dumped from the system, whether the water is dumped by means of bleed-off or blow-down, by as much as 95% over conventional cooling tower systems. This is equivalent to a 30% reduction in the total water consumption for the process. As a result, significant savings in operating costs are realized. In addition, utilization of the chemical additives described above significantly reduces the fouling of the cooling tower system; so that more efficient operation takes place, and longer life of all of the system components results. This equates to additional significant savings.

1:1 SOAP CHEMICAL CONSTITUENT STUDIES

1. Cooling Tower Chemistry Considerations

Cooling towers are normally scaled and feed water also contains "basic" chemicals such as calcium and magnesium carbonates, bicarbonates, hydroxides, etc. In the chemistry studied there is (1) free hydroxacetic acid (HOAcOH) which gives the compositions a pH of about 3, (2) a 1:1 soap or quaternary ammonium compound between triethanolamine (TEA) and hydroxacetic acid, i.e. [TEAH]+[OAcOH]−, where the hydrogen ion or proton has transferred from the hydroxacetic acid to the free electron pair on the nitrogen and (3) sodium xylene sulfonate (SXS). When the composition is added to cooling towers, the excess hydroxyacetic acid present reacts rapidly with the scale and/or calcium and magnesium compounds, etc. in solution to form the corresponding calcium, magnesium, etc. soaps which are much more soluble than the scale and inorganic carbonates, etc. The operating pH range of the cooling tower continues in the range of 9 to 6.5 because the free hydroxyacetic acid has been consumed.

According to the above identified applications, the 1:1 soap is the reaction product of a weak organic acid and a weak amine base which inherently is in equilibrium with low levels of free hydroxyacetic acid and triethanolamine. This equilibrium allows for free hydroxyacetic acid to be generated, even under basic conditions, which in turn can react with inorganic carbonates, etc. for continued protection of the tower against scale formation.

2. ORP Studies on Chemical Species

In the ORP studies that follow, it was of interest to determine the effect on ORP readings for hydroxyacetic acid, triethanolamine, sodium xylene sulfonate, the hydroxyacetic ion and the 1:1 neutral soap between triethanolamine and hydroxyacetic acid. The results of these studies were conducted in "conditioned" tap water (i.e., boiled and stirred until ORP leveled off).

HYDROXYACETIC ACID

The results indicate that hydroxyacetic acid has the greatest effect on ORP increasing it some 220 units when present in over 0.04% wt. Hydroxyacetic acid, as such, would not be present in an operating cooling tower since it is rapidly consumed by reaction with the scale, etc. present.

1:1 SOAP OF TRIETHANOLAMINE AND HYDROXYACETIC ACID

The lowest level of 0.01% wt. for this 1:1 soap gave an increase in the ORP of about 30 units and remained essentially constant with increasing concentration up to 0.20% wt. This indicates that low levels of this 1:1 soap can be detected by ORP.

It is important to determine if the ORP is detecting the triethanolammonium ion, [TEAH]+, or the hydroxyacetic ion, [OAcOH]−, particularly in the pH range of 9 to 6.5 for cooling tower operation.

SODIUM HYDROXYACETATE

A neutral solution of sodium hydroxy acetate was prepared and added to the ORP test solution. The ORP essentially did not change with the addition of sodium hydroxyacetate. The presence of the hydroxyacetate ion does not effect the ORP reading. Also, it is well known that the sodium ion does not have an effect on ORP.

The increase in ORP for this 1:1 soap is therefore attributed to the triethanolammonium ion, [TEAH]+. This ionic species can exist in the pH range of 9 to 6.5 in cooling towers. As long as it's presence can be detected there will be hydroxyacetic acid available via the equilibrium discussed above, which can then control the scale forming tendencies in the system. When it can no longer be detected, the ORP meter will call for additional soap.

SODIUM XYLENE SULFONATE

Sodium xylene sulfonate, the reaction product of a strong acid and a strong base, has no effect on ORP when added up to 0.20% wt. in this study.

TRIETHANOLAMINE

The addition of triethanolamine, which is 85% triethanolamine and 15% diethanolamine, decreases the ORP reading somewhat with increase in concentration. In earlier work, TEA was found to be very low in conductivity in aqueous solutions. Although TEA is a weak base, it will increase the pH of an aqueous solution to about 9 by reacting with water to form low levels of hydroxide ion. It was earlier demonstrated that ORP is very sensitive to changes in pH in the range of pH=9 to 6. For this reason it was not unexpected that TEA would decrease the ORP slightly in this test.

OTHER 1:1 SOAPS

Several other neutral soaps of weak organic acids with triethanolamine were prepared and added to conditioned tap water to determine the effect on ORP. The results are summarized in Table A.

TABLE A

| ACID | ORP INCREASE |
| --- | --- |
| Hydroxyacetic | 30 |
| Acetic | 28 |
| Citric | 26 |
| Benzoic | 27 |

It appears that the 1:1 soaps of weak acids and weak bases (amines) result in essentially the same increase in ORP. This is expected as the same triethanolammonium ion, [TEAH]+, is present in all the soaps tested. Other amines include morpholine imidazole, 3-picoline and diethylamine.

TITRATION CURVE STUDIES OF A 1:1 SOAP OF AN ORGANIC ACID AND AMMONIA

A new experiment was designed to further simulate cooling tower applications of the chemistry. Ammonia was added to about one liter of conditioned tap water (or acidified conditioned tap water as noted) with vigorous stirring. An ORP reading was then taken when stabilized.

Organic acids were then added in small increments with vigorous stirring. The experiments were modeled after the triethanolamine/hydroxyacetic acid soaps and employed the same relative equivalents so that the curves can be compared on a nearly equivalent basis. The ORP of the solution was measured over a period of 5 to 15 min. after the addition and an average ORP taken as the plot point. During the addition of the acid the corresponding "ammonium" ion is formed by reaction of the acid with ammonia which increases the ORP measurement. The following titration curve studies were conducted:

1. 1:1 Soap of Ammonia and Hydroxyacetic Acid

Ammonium hydroxide, also a very strong inorganic nitrogen base, when added to acidified conditioned tap water, also results in a large ORP drop and a high pH.

A very large increase in ORP with the addition of hydroxyacetic acid is noted over the pH range of 12 to 7 due to the higher concentration of the "ammonium" ion of the 1:1 soap which is formed with the equilibrium shifted toward the 1:1 soap because of the strong base.

2. 1:1 Soap of Ammonia and Benzoic Acid

Tap water was conditioned by simply stirring overnight and the ORP leveled about 170 units and the pH was 6 as determined by litmus paper. Upon addition of the ammonia, the ORP dropped to 50, the pH was 9 and the solution became cloudy from the hard water components as expected. Upon incremental addition of the benzoic acid the ORP increased linearly with increased amount of ammonium ion (soap) formation. As the pH became acidic the precipitate dissolved as expected. A little more benzoic acid was required to give the rapid rise in ORP due to the presence of hard water components present in the stirred conditioned tap water.

3. 1:1 Soap of Ammonia and p-Toluenesulfonic Acid

Acidified condition tap water was employed. Upon addition of the ammonia the ORP dropped 102 units and pH was again 9. Upon incremental addition of the p-toluenesulfonic acid the ORP again rose linearly over the basic pH range and sharply rose and leveled over the acidic pH range. Again, ORP is sensitive to the concentration of the ammonium ion (soap) present.

The foregoing description of the preferred embodiment of the invention should be considered as illustrative, and not as limiting. For example, although the embodiment described is used with a cooling tower, the system also may be used for water purification systems (distillation), reverse osmosis, etc., closed heat exchange systems (automotive radiators), swimming pools, water distribution systems, and industrial systems. Various other uses, changes and modifications will occur to those skilled in the art, without departing from the true scope of the invention as defined in the appended claims.

What is claimed is:

1. An automatic control system adapted for controlling scale formation in a water circulating system comprising:

first sensing means for measuring the oxygen reduction potential (ORP) of the circulating water containing a soap having a 1:1 stoichiometric equivalent of an organic acid and ammonia in the water for controlling scale formation in said system and supply means for automatically supplying said soap in response to a predetermined ORP measured by said first sensing means substantially corresponding to a pH higher or lower than a selected range for controlling said scale.

2. The system according to claim 1 further including:

second sensing means for measuring the conductivity of the water as a factor of total dissolved solids (TDS) in the water and means coupled with said second sensing means for removing water in response to the measurement of a predetermined conductivity of the water by said second sensing means.

3. The system according to claim 2 wherein said means for removing water removes a predetermined quantity of water from the system in response to the measurement of a predetermined conductivity of such water by said second sensing means.

4. The system according to claim 2 wherein said means for removing water includes a normally-closed drain valve means; and means for opening said normally-closed drain valve means for a predetermined time interval in response to the measurement of said predetermined conductivity of the water by said second sensing means.

5. The system according to claim 4 further including biocidal feeder means being coupled with said second sensing means for supplying biocidal chemicals to said water in response to the measurement of said predetermined conductivity of said water by said second sensing means.

6. The system according to claim 1 wherein the water is recirculated by a pump through a recirculating conduit, and said first sensing means senses the soap in water supplied through the conduit by the pump.

7. The system according to claim 6 further including:

a shunt conduit coupled across at least a portion of the recirculating conduit so that said first sensing means senses the soap in water flowing through said shunt conduit.

8. The system according to claim 1 wherein said soap in said supply means is in liquid form, and further including a pump for removing said soap from said supply means to supply said soap to said water, said pump being coupled with said first sensing means and operated in response to the sensing of the predetermined ORP measured by said first sensing means.

9. The system according to claim 1 wherein said soap in said supply means is in liquid form, and further including a pump for removing soap from said supply means and for supplying said soap to said water, said pump coupled with said first sensing means and operated in response to the sensing of a predetermined ORP measured by said first sensing means.

10. The system according to claim 1 wherein the organic acid is a carboxylic or sulfonic acid.

11. The system according to claim 10 wherein the organic acid is selected from the group consisting of hydroxyacetic, acetic, citric and benzoic, and mixtures thereof.

* * * * *